United States Patent [19]
Ryan et al.

[11] Patent Number: 5,456,284
[45] Date of Patent: Oct. 10, 1995

[54] ELASTOMERIC VALVE ASSEMBLY

[75] Inventors: Timothy C. Ryan, Laguna Hills; Charles C. Hart, Huntington Beach; Mark A. Ritchart, Murrieta; Donald L. Gadberry, San Juan Capistrano, all of Calif.

[73] Assignee: Applied Medical Resources Corporation, Laguna Hills, Calif.

[21] Appl. No.: 59,804

[22] Filed: May 10, 1993

[51] Int. Cl.$^6$ .............................. F16K 15/14; A61B 1/01
[52] U.S. Cl. ..................... 137/522; 600/159; 604/167; 604/256
[58] Field of Search .................... 137/317, 522, 137/846, 847, 850; 128/4, 4 A; 251/339; 604/167, 256

[56] References Cited

U.S. PATENT DOCUMENTS

| | | | |
|---|---|---|---|
| 2,710,623 | 6/1955 | Kolos | 137/847 |
| 3,504,699 | 4/1970 | Grise | 137/846 |
| 3,517,682 | 6/1970 | Smith | 137/846 |
| 4,341,239 | 7/1982 | Atkinson | 137/846 |
| 4,436,519 | 3/1984 | O'Neill | 604/256 |
| 4,524,805 | 6/1985 | Hoffman | 137/846 |
| 4,535,819 | 10/1985 | Atkinson et al. | |
| 4,566,493 | 1/1986 | Edwards et al. | |
| 4,612,960 | 9/1986 | Edwards et al. | 137/846 |
| 4,649,904 | 3/1987 | Krauter et al. | 604/167 |
| 4,715,360 | 12/1987 | Akui et al. | 604/256 |
| 5,114,408 | 5/1992 | Fleischhaker et al. | 604/256 |

Primary Examiner—George L. Walton
Attorney, Agent, or Firm—Richard L. Myers

[57] ABSTRACT

A medical access device is adapted to receive an instrument and comprises a housing defining an inner channel and a valve disposed in the channel to form a seal with the housing. The valve includes an outer wall and a pair of inner walls extending in distally converging relationship to define a slot. At least one compression member extends between the outer wall and an associated one of the inner walls. The compression member is compressed in response to insertion of the instrument and exerts a force on the associated inner wall when compressed to reduce leakage of the valve when the instrument is inserted. A funnel is provided at the distal end of the valve to facilitate backloading of the instrument.

17 Claims, 3 Drawing Sheets

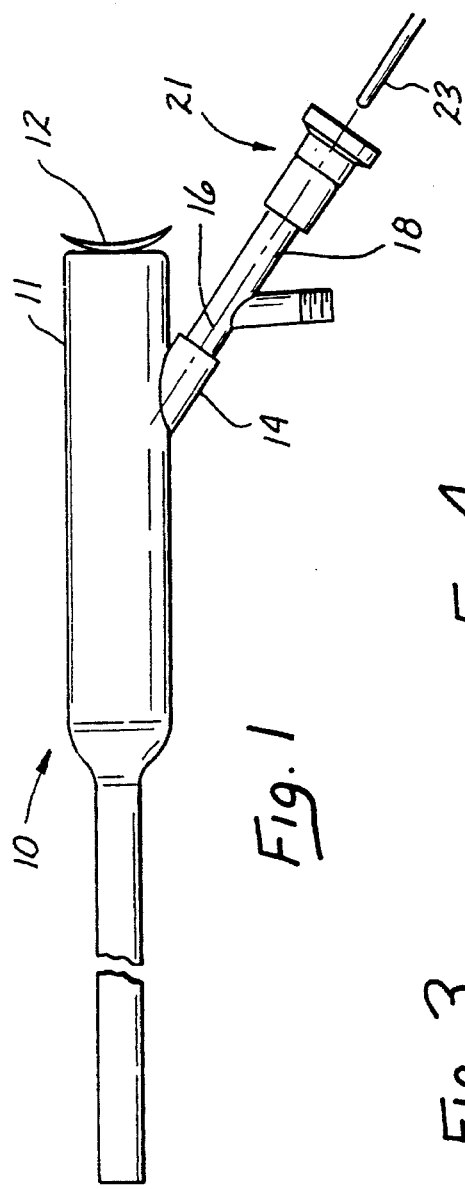
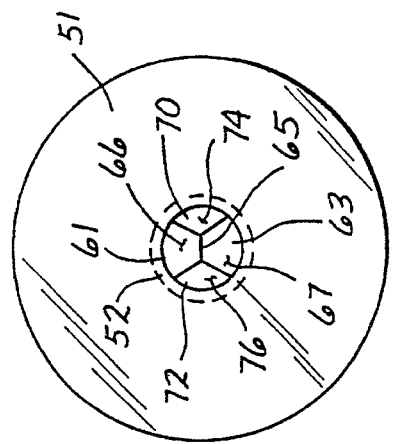
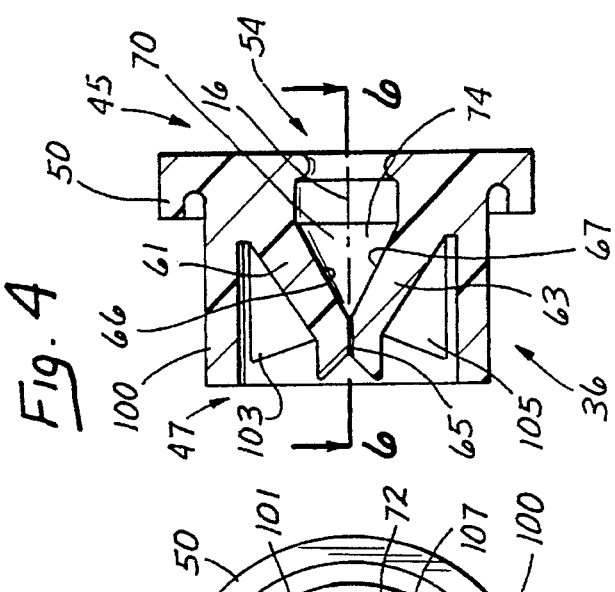
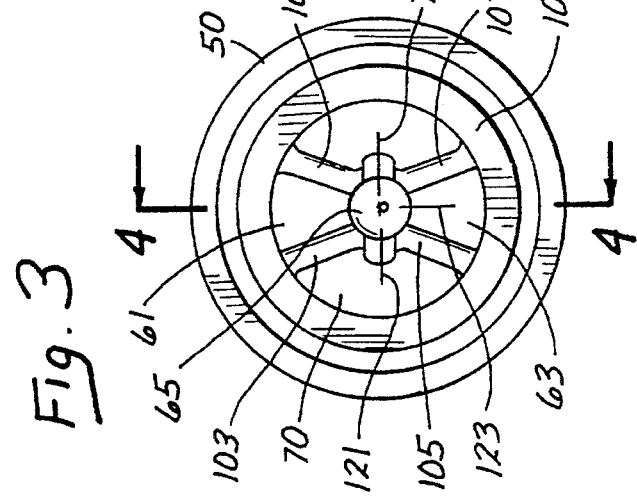

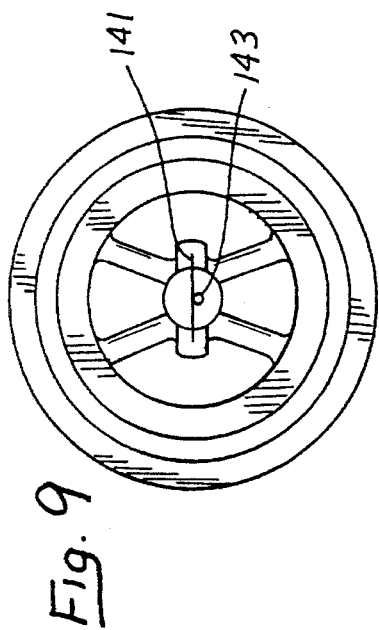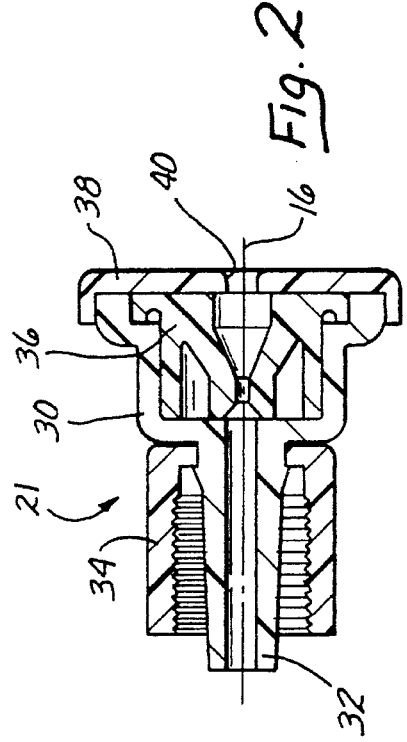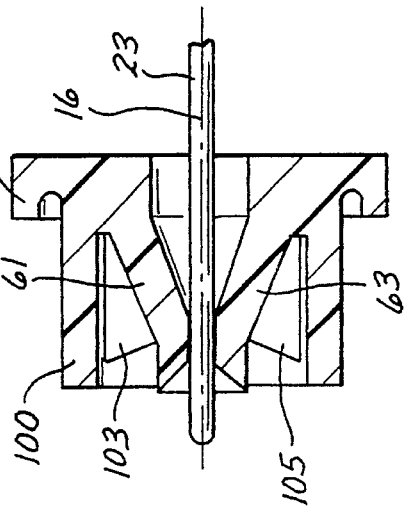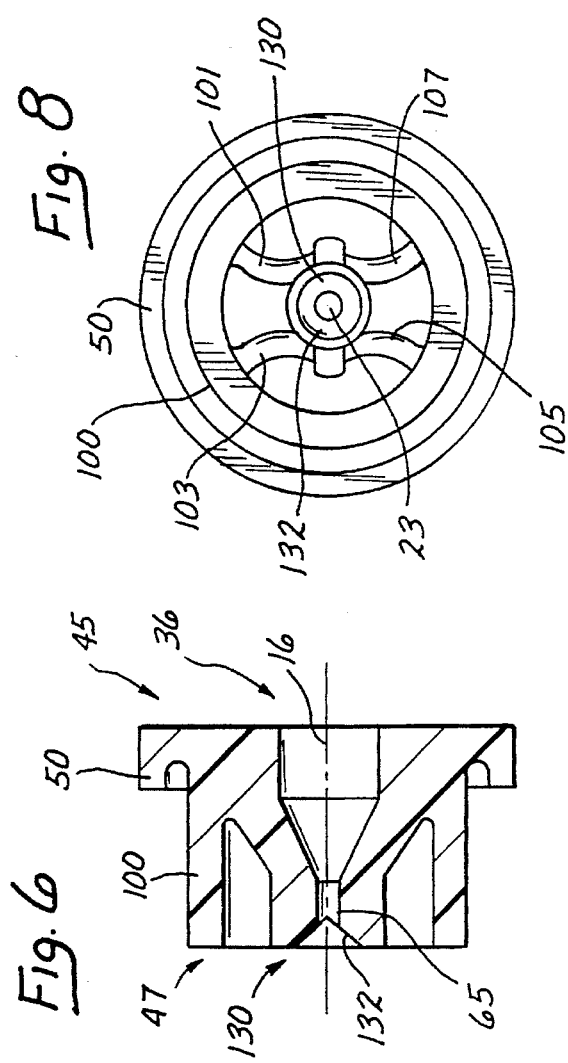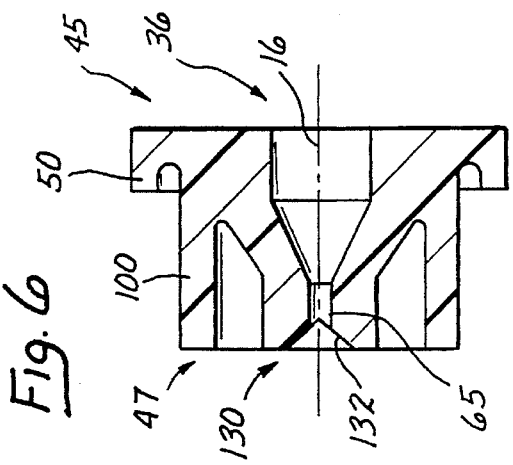

ELASTOMERIC VALVE ASSEMBLY

BACKGROUND OF THE INVENTION

1. Field of the Invention

This invention relates generally to elastomeric fluid control valves and more specifically to valves having a duck bill configuration.

2. Discussion of the Prior Art

Elastomeric valves are commonly used to control the flow of fluids. Valves of particular interest to the present invention are formed from a pair of walls, each having a generally planar configuration, which converge and intersect along a line or slot. With this configuration, these valved are commonly referred to as "duck bill" valves.

The duck bill valves are particularly adapted to enable fluid flow in one direction while inhibiting fluid flow in the opposite direction. These characteristics are particularly appreciated in surgical access devices which control the flow of fluids such as blood (in the case of endoscopes) or gasses (in the case of trocars).

The duck bill valves of the past have not been particularly suited for use as valves in those environments where surgical instruments are to be inserted through the valve. In these cases, valve is required to form a seal with the outer surface of the access device in order to maintain a gas or fluid pressure at the distal end of the device. When an instrument is inserted into a duck bill, it passes between the converging walls of the valve and through the slot at the distal end of the valve. This causes the walls to separate and to create an undesirable flow channel between the slot and the instrument. This phenomena is commonly referred to as the "cat-eye" effect.

In some case valves have been used with endoscopes wherein guidewires have been inserted through the valves. Where a particular procedure demands that the endoscope be removed leaving the guidewire in place, reinsertion of the endoscope over the guidewire has required backloading of the valve. Such backloading is particularly difficult with duck bill valves since the distal end of the valve is configured only with the narrow shape of the slot.

For these reasons the duck bill valves of the past have not been suitable for use in medical access devices particularly when such a device must accommodate insertion and removal of a surgical instrument.

SUMMARY OF THE INVENTION

In accordance with the present invention, a duck bill valve is provided with a cylindrical outer wall and compression elements which extend from the outer wall to engage a pair of inner walls which form the duck bill. These compression elements are disposed to engage the inner walls at positions particularly chosen to reduce the cat-eye effect. When an instrument is inserted into the valve, these elements are placed in compression and create a force on the inner walls which greatly reduces the cross sectional area of the undesirable flow channel. With a greatly reduced "cat-eye" effect, these duck bill valves, with their excellent fluid flow characteristics, are particularly adapted to accommodate insertion of an instrument. Providing the slot with a "T" shaped configuration in radial cross section also decreases the cat-eye effect particularly when the instrument inserted is quite small.

In a preferred embodiment of the invention, the valve is formed with a funnel at its distal end which facilitates backloading of an instrument such as a guidewire. The guidewire is inserted into the distal end of the access device and moved into contact with the funnel which guides the wire toward and through the slot of the valve.

In one aspect of the invention, a valve having an axis extending between a proximal end and a distal end includes a cylindrical outer wall and a pair of inner walls which converge distally to intersect at a slot formed between the inner walls. When an instrument is inserted between the inner walls and through the slot, the inner walls have a tendency to form an undesirable leakage channel around the instrument. At least one compression member extends between the cylindrical outer wall and an associated one of the inner walls. This compression member is adapted to compress in response to insertion of the instrument and to exert a force on the associated inner wall when compressed to reduce the cross sectional area of the leakage channel.

In another aspect of the invention, the valve is divided by a first plane and a second plane which intersects the first plane along an axis of the valve. The valve comprises a cylindrical outer wall and a pair of inner walls which extend toward each other in distally converging relationship to define a slot in proximity to the distal end of the valve. The slot, with a major portion extending in the first plane and a minor portion extending in the second plane, is adapted to form a seal around the instrument.

In still a further aspect of the invention, portions of the inner walls define a slot in a plane including the axis of the valve. The valve also includes a funnel having an inner surface which converges between the distal end of the valve and the slot, to guide the instrument toward the slot when the instrument is backloaded into the valve.

The invention also includes a method for backloading a surgical instrument into an access device. The method includes the steps of providing the device with a valve having a pair of walls which converge distally to intersect along a slot in a duck bill configuration, and providing a funnel at the distal end of the valve with an inner surface which converges toward the slot. The method further comprises the steps of inserting the instrument distally into the valve, and removing the access device distally from the instrument.

Then the instrument is inserted proximally into the distal end of the slot engaging the inner surface of the funnel to guide the instrument into the slot and proximally through the valve thereby backloading the instrument into the access device.

These and other features and advantages of the invention will be more apparent with the description of preferred embodiments and reference to the associated drawings.

DESCRIPTION OF THE DRAWINGS

FIG. 1 is a side elevation view of an endoscope including a valve assembly of the present invention;

FIG. 2 is an axial cross section view of a preferred embodiment of the valve assembly;

FIG. 3 is an enlarged distal end view of a valve illustrated in FIG. 2;

FIG. 4 is an axial cross section of the valve taken along lines 4—4 of FIG. 3;

FIG. 5 is a proximal end view of the valve illustrated in FIG. 4;

FIG. 6 is an axial cross section view of the valve taken along lines 6—6 of FIG. 4;

FIG. 7 is an axial cross section view similar to FIG. 4 and illustrating an instrument inserted through the valve;

FIG. 8 is a distal end view similar to FIG. 3 and showing the instrument inserted through the valve of FIG. 7;

FIG. 9 is an end view similar to FIG. 3 of a further embodiment of the invention wherein a slot of the valve has a T-shaped configuration;

DESCRIPTION OF PREFERRED EMBODIMENTS AND BEST MODE OF THE INVENTION

Figure 4A:
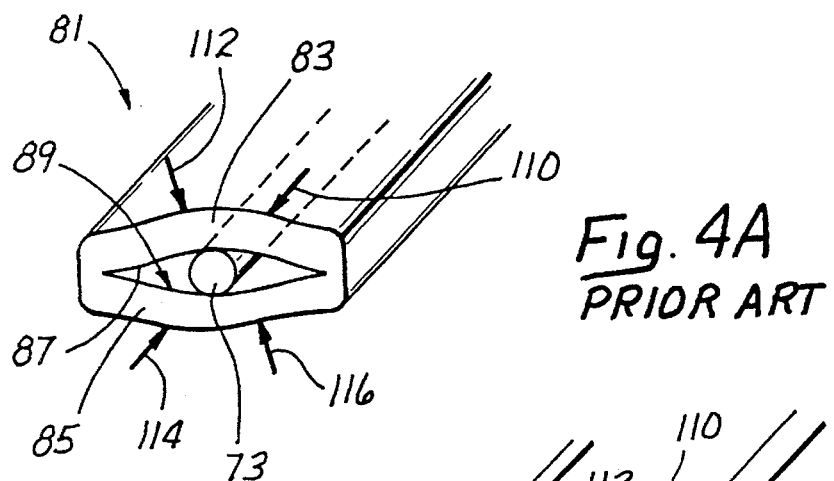
FIG. 4A is an enlarged distal end view of a duck bill valve of the prior art illustrating an undesirable flow channel.

An endoscope is illustrated in FIG. 1 and designated generally by the reference numeral 10. This endoscope 10 is representative of any access device or other surgical apparatus which needs to control the flow of a fluid, either liquid or gas, along a channel. The endoscope 10 includes a tubular body 11 which includes an eye cup 12 at its proximal end, as well as a working channel and visualization channel coaxially disposed within the tubular body 11, as is well known in the art. The port 14 has an axis 16 which extends through a Y-fitting 18 and a valve assembly 21 of special interest to the present invention. This valve assembly 21 is particularly adapted to receive an elongate surgical instrument, such as a guidewire 23. When the guidewire 23 is inserted into the endoscope, it extends though the valve assembly 21, along the axis 16, through the side port 14, and into the working channel of the endoscope 10.

The valve assembly 21 is best illustrated in FIG. 2 where it is shown to include a valve housing 30 having an elongate nose 32 which fits into the Y-fitting 18. A sleeve 34 is snap fit over the nose 32 and internally threaded to register with threads on the Y-fitting 18. Rotation of the sleeve 34 secures the valve assembly 21 to the Y-fitting 18. A valve 36 of particular interest to the present invention is disclosed within the housing 30 and held in that location by a cap 38 which can be snap fit or screwed onto the housing 30. An aperture 40 in the cap 38 is positioned along the axis 16 and provides access into the valve assembly 21 and the working channel 13 of the endoscope 10.

The valve 36 is of the type commonly referred to as a "duck bill" valve. This valve is best illustrated in the enlarged views of FIGS. 3, 4, and 5 to have a proximal end 45 and a distal end 47. The proximal end is provided with an annular flange 50 which has a proximal surface 51. In this embodiment, the flange 50 forms a seal with the inner surface of the housing 30 as it is compressed between the housing 30 and the cap 38. The flange 50 includes an annular lip 52 which defines a hole 54 along the axis 16. This hole 54 provides access into the valve 36 for the instrument, such as the guidewire 23.

The duck bill valve 36 is defined primarily by a pair of walls 61 and 63 which may have a generally planar configuration. These walls 61 and 63 converge distally toward the axis 16 where they intersect along a slot 65. The slot 65 will typically be defined by the walls 61, 63 in a plane which includes the axis 16.

In a preferred embodiment the generally planar walls 65 and 63 having respective inner surfaces 66 and 67, are connected by generally conical walls 70 and 72 having respective inner surfaces 74 and 76. These walls 70 and 72 also converge toward the slot 65 so that in combination the walls 61, 63, 70 and 72 form an enclosure which funnels the instrument 23 toward the slot 65 as it passes from the proximal end 45 to the distal end 47.

It is unusual that a duck bill valve would be used in an environment which must accommodate the insertion of instrument. A duck bill valve 81 of the prior art is shown in FIG. 4A and best illustrates this problem. This valve 81 also includes a pair of planar walls 83 and 85 which are similar to the walls 61 and 63. These walls converge to form a slot 87 which is similar to the slot 65. In the past, when an instrument such as the guidewire 23 was inserted into the valve 81, the walls 83 and 85 tended to separate. The wall portions defining the slot 87 also separated in order to accommodate the instrument 23. This separation was advantageous in that it enabled the instrument 23 to be inserted through the valve 81, but it also tended to form an undesirable fluid channel 89 which permitted the escape of fluids. This formation, commonly referred to as the "cat-eye" effect was thought to be so intolerable that duck bill valves were thought to be inappropriate for the accommodation of instrument insertion.

In accordance with the present invention, the valve 36 is provided with an outer wall 100 which is formed as a continuous surface about the axis 16. In a preferred embodiment the outer wall 100 is a surface of rotation about the axis 16 and has the configuration of a cylinder. Extending inwardly from the outer wall 100 are a plurality of compression elements designated by the reference numerals 101–107. In a preferred embodiment, these elements 101–107 are disposed in respective planes which are parallel to the axis 16 but intersect the slot 65 at respective locations each of which is removed from the axis 16. More specifically, the compression elements 101–107 are positioned so that their respective planes are directed toward the enlarged areas which form the fluid channel 89 and produce the undesirable cat-eye effect. The planes of the elements 101–107 might be oriented for example along the four arrows in FIG. 4A and designated by the even reference numerals 110–116.

Figure 4B:
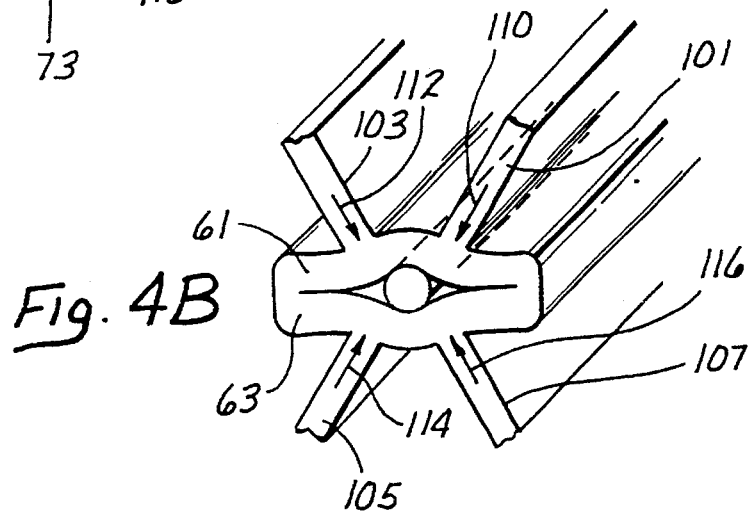
FIG. 4B is a distal end view of a duck bill valve of the present invention including a plurality of compression elements which reduce the size of the undesirable flow channel.

FIG. 4B shows the valve 36 of the present invention in a form which is similar to that of FIG. 4A. In the view of FIG. 4B, the compression elements 101–107 are formed in planes including the respective arrows 110–116. As the instrument, such as the guidewire 23, is inserted into the valve 36 as illustrated in FIG. 7, the elements 101–107 are placed in compression and tend to buckle as illustrated in FIG. 8. When in the compressed state, the elements 101–107 exert a force generally along the arrows 110–116 which presses against the walls 61 and 63 thereby tending to close the undesirable fluid channel 89. This highly desirable result is illustrated in FIG. 4B. With the compression elements thus positioned, the duck bill valve 36 overcomes the problems of the past making it possible to accommodate instrument insertion without sacrificing its superior fluid flow characteristics.

Referring again to FIG. 3, the valve 36 can be divided into quadrants defined by a horizontal plane 121 which may include the slot 65, and a vertical plane 123 intersecting the plane 121 along the axis 16. With this basis for orientation, it can be seen in the preferred embodiment, that compression elements 101–107 are each disposed in an associated quadrant of the axis 16.

The purpose of the outer wall 100 is to provide a structure against which the compression elements 101–107 can be compressed to provide the desired force against the walls 61 and 63. It will be apparent that in a particular embodiment, the outer wall 100 could be eliminated and the compression elements 101 and 107 closely spaced relative to the valve housing 30. Alternatively, the compression elements 101–107 could be disposed to extend between the annular flange 50 and the walls 61 and 63. It should be clear that the compression elements 101 and 107 require some structure against which they can be compressed as the walls 61 and 63 are forced outwardly by the instrument 23. While that structure might benefit from an axial orientation and close proximity to the wall 61 and 63, such as the outer wall 100, these features may not be of as much importance in a particular embodiment.

Figure 9A:
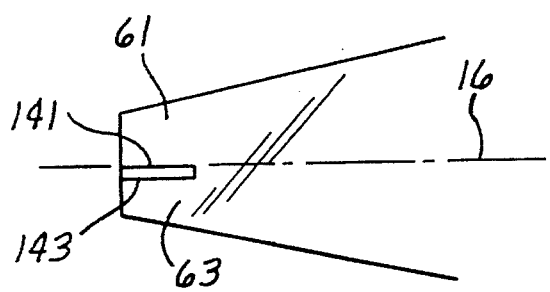
FIG. 9A is an axial cross section view of the valve taken along lines 9a—9a of FIG. 9.

Closure of the undesirable fluid channel 89 can also be enhanced, particularly for smaller diameter instruments such as the guidewire 23, with a special configuration of the slot 65, best illustrated in FIG. 9. In this embodiment of the valve 36, the slot 65 has a major portion 141 which extends horizontally in the illustrated embodiment and a minor portion 143 which extends vertically and intersects the major portion 141 at the axis 16. Thus the slot 65 in this embodiment has a generally T-shaped or X-shaped configuration. In a preferred embodiment, the major portion 141 of the slot 65 has a length along the axis 16 which is less than the width of the portions 141. In contradistinction, the length of the minor portion 143 along the axis 16 is greater than the height of the minor portion 143. In other words, the extension of the slot 65 along the axis 16, is greater than the height of the minor portion 143 but less than the width of the major portions 141.

Figure 9B:
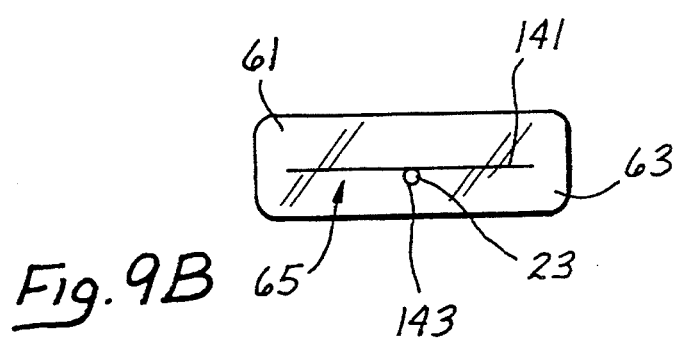
FIG. 9B is an enlarged distal end view of the valve of FIG. 9, illustrating a small diameter instrument inserted through the T-shaped slot.

This configuration is particularly desirable for small diameter instruments 23 and provide for a reduced cat-eye effect. As illustrated in FIG. 9B, this configuration of the slot 65 will accommodate the instrument 23 slightly off-axis with better sealing characteristics than those provided by a planar slot 65.

Under some circumstances it is desirable to remove the access device, such as the endoscope 10, from the guidewire 23 once it has been inserted. This is typically accomplished by engaging the guidewire 23 distally of the endoscope 10 and pulling the endoscope off of the proximal end of the guidewire 23. This procedure leaves the guidewire 23 in place thereby permitting other surgical instruments to be inserted over the guidewire 23. In some cases, the endoscope 10 may need to be reinserted over the guidewire 23 to provide for further visualization at the surgical site. This requires that the proximal end of the guidewire 23 be inserted into the distal end of the working channel of the endoscope 10. Since this working channel extends through the side port 14, the guidewire is then directed proximally through the side port 14, the Y-fitting 18, and the valve assembly 21.

In order to accommodate the backloading of the guidewire 23, the distal end 47 of the valve 36 can be provided with a funnel structure 130 having an inner surface 132 which converges proximally as it approaches the slot 65. Thus the surface 132 decreases radially with progressive proximal positions along the axis 16.

The valve 36 will typically be formed as a single unit with materials having elastomeric characteristics. Alternatively, the valve might be formed from other materials as long as at least the walls 61, 63 and the compression elements 101–107 are formed from elastomeric materials. In a particular embodiment it may also be possible to position the slot 65 so that it is removed from the axis 16. The compression elements 101–107 may have other than a planar configuration and may be positioned along the slot 65 to provide the best orientation for a particular instrument, such as the guidewire 23. As noted, the slot 65 can be configured in a single flat plane or provided with alternative configurations such as the T-shape or the X-shape in order to further facilitate closure of the undesirable fluid channel 89.

Given these wide variations, which are all within the scope of this concept, one is cautioned not to restrict the invention to the embodiments which have been specifically disclosed and illustrated, but rather encouraged to determine the scope of the invention only with reference to the following claims.

We claim:

1. A valve adapted to receive a surgical instrument and having an axis extending between a proximal end and a distal end of the valve, comprising:

an outer wall extending between the proximal end and the distal end of the valve;

a pair of inner walls extending between the distal end and the proximal end of the valve and converging distally to intersect at a slot formed between the inner walls, the inner walls having a tendency to separate when the instrument is inserted between the inner walls and through the slot, and to form an undesirable leakage channel having a cross-sectional area around the instrument; and at least one compression member extending between the outer wall and an associated one of the inner walls, the compression member being adapted to compress in response to insertion of the instrument and to exert a force on the associated inner wall when compressed to reduce the cross-sectional area of the leakage channel.

2. The valve recited in claim 1 further comprising:

a funnel having an inner surface which converges proximally between the distal end of the valve and the slot to guide the instrument toward the slot when the instrument is backloaded into the valve from the distal end to the proximal end of the valve.

3. The valve recited in claim 1 further comprising four separate compression members each disposed in a separate quadrant of the axis of the valve.

4. The valve recited in claim 3 wherein:

each of the compression members is disposed at a particular angle to the slot; and the particular angles of the compression members are substantially equal.

5. The valve recited in claim 1 wherein:

the valve is divided into quadrants defined by a horizontal plane and a vertical plane which intersects the horizontal plane at the axis of the valve;

the slot is defined by a major portion which extends in the horizontal plane and a minor portions which extends in the vertical plane to provide the slot with a T-shaped configuration in radial cross section.

6. The valve recited in claim 1 wherein the compression member is disposed generally in a plane when not compressed and the plane of the compression member intersects the slot at other than the axis of the valve.

7. The valve recited in claim 1 wherein the outer wall is generally cylindrical in configuration.

8. The valve recited in claim 1 and being divided by a first plane and a second plane which intersects the first plane along the axis of the valve, wherein the slot formed between the inner walls of the valve has a major portion extending in the first plane of the valve and a minor portion extending in the second plane of the valve.

9. The valve recited in claim 8 wherein:

the major portion of the slot has a width disposed along the axis of the valve and a length transverse to the axis of the valve;

the length of the major portion of the slot is greater than the width of the major portion of the slot;

the minor portion of the slot has a length along the axis of the valve and a width transverse to the axis of the valve; and the length of the minor portion of the slot is greater than the width of the minor portion of the slot.

10. A surgical apparatus comprising a valve adapted to receive a surgical instrument which has a distal end and a proximal end, for insertion into a surreal site, said valve having an axis extending between a proximal end and a distal end of the valve, the valve comprising:

a pair of generally planar inner walls extending between the distal end and the proximal end of the valve and converging distally to intersect at a predetermined location along the axis;

portions of the inner walls defining a slot in a plane including the axis at a location proximate to said predetermined location; and a funnel structure having an inner surface which converges proximally from the distal end of the valve to the slot, said funnel structure being adapted to guide the proximal end of the instrument toward the slot when the instrument is inserted into the surreal apparatus and then through the valve in a backwards direction from the distal end of the valve to the proximal end of the valve.

11. The valve recited in claim 10 wherein the inner walls are configured to separate when the instrument is inserted into the valve and through the slot, and to form an undesirable leakage channel with a cross-sectional area around the instrument, the valve further comprising:

a cylindrical outer wall; and at least one compression member extending between the cylindrical outer wall and an associated one of the inner walls, the compression member being adapted to compress in response to insertion of the instrument and to exert a force on the associated inner wall when compressed to reduce the cross-sectional area of the leakage channel.

12. The valve recited in claim 10 wherein:

the valve is divided into quadrants defined by a first plane and a second plane which intersects the first plane along the axis; and the slot includes a major portion which is disposed in the first plane and a minor portion which is disposed in the second plane to provide the slot with a T-shaped configuration in radial cross section.

13. The valve recited in claim 10 wherein the inner walls are configured to separate when the instrument is inserted into the valve and through the slot, and to form an undesirable leakage channel with a cross-sectional area around the instrument, the valve further comprising:

at least one compression member extending outwardly from an associated one of the inner walls, the compression member being adapted to deform in response to insertion of the instrument and to exert a force on the associated inner wall when deformed to reduce the cross-sectional area of the leakage channel.

14. A medical access device adapted to receive an instrument, comprising:

a housing having walls defining an inner channel;

a valve disposed in the channel and forming a seal with the walls of the housing, the valve having an axis extending between a proximal end and a distal end of the valve;

an outer wall of the valve extending between the proximal end and the distal end of the valve, the outer wall comprising a surface of revolution around the axis of the valve;

a pair of inner walls included in the valve and extending between the distal end and the proximal end of the valve in distally converging relationship to intersect at a slot, the inner walls having a tendency to separate when the instrument is inserted into the access device between the inner walls and through the slot, and to form an undesirable leakage channel having a cross sectional area around the instrument; and at least one compression member extending between the outer wall and an associated one of the inner walls, the compression member being adapted to compress in response to insertion of the instrument and to exert a force on the associated inner wall when compressed to reduce the cross sectional area of the leakage channel.

15. The valve recited in claim 14 and being divided by a first plane and a second plane which intersects the first plane along the axis of the valve, wherein the slot formed between the inner walls of the valve has a major portion extending in the first plane of the valve and a minor portion extending in the second plane of the valve.

16. The valve recited in claim 15 wherein:

the major portion of the slot has a width disposed along the axis of the valve and a length disposed transverse to the axis of the valve;

the length of the major portion of the slot is greater than the width of the major portion of the slot;

the minor portion of the slot has a length along the axis of the valve and a width transverse to the axis of the valve; and the length of the minor portion of the slot is greater than the width of the minor portion of the slot.

17. A method for backloading a surgical access device onto a surgical instrument, a distal end of which is disposed at a surgical site, the access device including a valve having a pair of walls extending between a distal end of the valve and a proximal end of the valve, the walls converging distally to intersect along a slot, and further including a funnel structure at the distal end of the valve, the funnel having an inner surface which converges proximally toward the slot, the method comprising the steps of:

contacting the inner surface of the funnel structure with the proximal end of the instrument, while the distal end of the instrument remains engaged distally of the valve, in proximity to a surgical site;

guiding a proximal end of the instrument proximally along the inner surface of the funnel structure and into the slot to form a seal between the valve and the instrument as the surgical access device moves along the instrument; and causing relative movement between the access device and the instrument so that the instrument is moved proximally between the walls of the valve as the surgical access device moves along the instrument.

* * * * *

UNITED STATES PATENT AND TRADEMARK OFFICE
CERTIFICATE OF CORRECTION

PATENT NO. : 5,456,284
DATED : October 10, 1995
INVENTOR(S) : Ryan et al.

It is certified that error appears in the above-identified patent and that said Letters Patent is hereby corrected as shown below:

Column 1, line 15, change "valved" to -- valve --.

Column 1, line 36, change "case" to -- cases --.

Column 3, line 53, delete "13".

Column 6, line 60, change "portions" to -- portion --.

Column 7, line 10, after the word "length" add the word -- disposed --.

Column 7, lines 22 and 36, change "surreal" to --surgical --.

Signed and Sealed this

Twenty-eighth Day of May, 1996

Attest:

BRUCE LEHMAN

Attesting Officer    Commissioner of Patents and Trademarks